US009017397B2

(12) United States Patent
Osborne et al.

(10) Patent No.: US 9,017,397 B2
(45) Date of Patent: Apr. 28, 2015

(54) VALVE DEVICE WITH INFLATABLE CHAMBER

(75) Inventors: Thomas A. Osborne, Bloomington, IN (US); Jacob A. Flagle, Indianapolis, IN (US); John A. Brumleve, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 294 days.

(21) Appl. No.: 13/493,563

(22) Filed: Jun. 11, 2012

(65) Prior Publication Data

US 2012/0253446 A1   Oct. 4, 2012

Related U.S. Application Data

(62) Division of application No. 11/394,303, filed on Mar. 30, 2006, now Pat. No. 8,197,534.

(60) Provisional application No. 60/666,791, filed on Mar. 31, 2005.

(51) Int. Cl.
*A61F 2/24* (2006.01)

(52) U.S. Cl.
CPC ............. *A61F 2/2418* (2013.01); *Y10T 29/494* (2015.01); *A61F 2/2409* (2013.01); *A61F 2/2475* (2013.01); *A61F 2/2412* (2013.01); A61F 2250/0003 (2013.01); A61F 2220/0008 (2013.01); A61F 2220/0016 (2013.01); A61F 2230/0026 (2013.01); A61F 2230/0095 (2013.01)

(58) Field of Classification Search
CPC ....... A61F 2/24; A61F 2/2409; A61F 2/2412; A61F 2/2418; A61F 2/2417; A61F 2250/0003

USPC ............. 623/1.25, 1.24, 1.26, 2.1, 2.11, 2.12, 623/2.17, 2.18, 2.19
See application file for complete search history.

(56) References Cited

U.S. PATENT DOCUMENTS

| 3,063,967 A | 11/1962 | Schultz |
| 3,063,968 A | 11/1962 | Schultz |
| 3,169,945 A | 2/1965 | Hostettler |
| 3,391,126 A | 7/1968 | Baggett et al. |
| 3,589,392 A | 6/1971 | Meyer |
| 3,912,692 A | 10/1975 | Casey et al. |
| 4,272,854 A | 6/1981 | Bokros |
| 4,731,074 A | 3/1988 | Rousseau et al. |
| 4,806,595 A | 2/1989 | Noishiki et al. |
| 4,872,875 A | 10/1989 | Hwang |
| 4,902,508 A | 2/1990 | Badylak et al. |
| 4,923,465 A | 5/1990 | Knoch et al. |
| 4,952,215 A | 8/1990 | Ouriel et al. |

(Continued)

*Primary Examiner* — David Isabella
*Assistant Examiner* — Suba Ganesan
(74) *Attorney, Agent, or Firm* — Buchanan Nipper

(57) ABSTRACT

Prosthetic valve devices for implantation in body vessels are provided. The prosthetic valve device includes at least one flexible member that permits fluid flow in a first direction and substantially prevents fluid flow in a second. The valve device also includes an inflatable chamber at least partially attached to the flexible member. The inflatable chamber is adapted to receive inflating media and is adapted to contact the body vessel. A delivery system is also provided that includes a valve device and a delivery apparatus. The delivery apparatus includes a member adapted for filling the chamber of the valve device with inflating media. A related method of making the valve device is also provided.

8 Claims, 6 Drawing Sheets

(56) References Cited

U.S. PATENT DOCUMENTS

| | | | |
|---|---|---|---|
| 5,080,670 A | 1/1992 | Imamura et al. |
| 5,108,425 A | 4/1992 | Hwang |
| 5,116,564 A | 5/1992 | Jansen et al. |
| 5,171,259 A | 12/1992 | Inoue |
| 5,178,632 A | 1/1993 | Hanson |
| 5,192,313 A | 3/1993 | Budd et al. |
| 5,275,826 A | 1/1994 | Badylak et al. |
| 5,281,422 A | 1/1994 | Badylak et al. |
| 5,370,685 A | 12/1994 | Stevens |
| 5,376,113 A | 12/1994 | Jansen et al. |
| 5,413,599 A | 5/1995 | Imachi et al. |
| 5,489,297 A | 2/1996 | Duran |
| 5,500,014 A | 3/1996 | Quijano et al. |
| 5,522,841 A | 6/1996 | Roby et al. |
| 5,554,185 A | 9/1996 | Block et al. |
| 5,609,598 A | 3/1997 | Laufer et al. |
| 5,707,389 A | 1/1998 | Louw et al. |
| 5,711,969 A | 1/1998 | Patel et al. |
| 5,713,920 A | 2/1998 | Bezwada et al. |
| 5,713,950 A | 2/1998 | Cox |
| 5,713,953 A | 2/1998 | Vallana et al. |
| 5,725,572 A | 3/1998 | Lam et al. |
| 5,733,337 A | 3/1998 | Carr, Jr. et al. |
| 5,741,327 A | 4/1998 | Frantzen |
| 5,824,063 A | 10/1998 | Cox |
| 5,855,601 A | 1/1999 | Bessler et al. |
| 5,879,382 A | 3/1999 | Boneau |
| 5,885,619 A | 3/1999 | Patel et al. |
| 5,895,420 A | 4/1999 | Mirsch, II et al. |
| 5,993,844 A | 11/1999 | Abraham et al. |
| 6,015,431 A | 1/2000 | Thornton et al. |
| 6,099,567 A | 8/2000 | Badylak et al. |
| 6,117,979 A | 9/2000 | Hendriks et al. |
| 6,126,686 A | 10/2000 | Badylak et al. |
| 6,178,968 B1 | 1/2001 | Louw et al. |
| 6,206,931 B1 | 3/2001 | Cook et al. |
| 6,254,636 B1 | 7/2001 | Peredo |
| 6,293,968 B1 | 9/2001 | Taheri |
| 6,312,474 B1 | 11/2001 | Francis et al. |
| 6,334,872 B1 | 1/2002 | Termin et al. |
| 6,344,052 B1 | 2/2002 | Greenan et al. |
| 6,375,989 B1 | 4/2002 | Badylak et al. |
| 6,379,710 B1 | 4/2002 | Badylak |
| 6,444,229 B2 | 9/2002 | Voytik-Harbin et al. |
| 6,458,153 B1 | 10/2002 | Bailey et al. |
| 6,503,272 B2 | 1/2003 | Duerig et al. |
| 6,572,650 B1 | 6/2003 | Abraham et al. |
| 6,585,761 B2 | 7/2003 | Taheri |
| 6,666,886 B1 | 12/2003 | Tranquillo et al. |
| 6,726,715 B2 | 4/2004 | Sutherland |
| 6,730,118 B2 | 5/2004 | Spenser et al. |
| 6,752,828 B2 | 6/2004 | Thornton |
| 2002/0099439 A1 | 7/2002 | Schwartz et al. |
| 2002/0123800 A1 | 9/2002 | Taheri |
| 2002/0138135 A1 | 9/2002 | Duerig et al. |
| 2003/0083741 A1 | 5/2003 | Woo et al. |
| 2003/0130726 A1 | 7/2003 | Thorpe et al. |
| 2003/0153972 A1 | 8/2003 | Helmus |
| 2003/0171824 A1 | 9/2003 | Abraham et al. |
| 2003/0191525 A1 | 10/2003 | Thornton |
| 2003/0195618 A1 | 10/2003 | Abraham et al. |
| 2003/0208261 A1 | 11/2003 | Thorpe et al. |
| 2003/0209835 A1 | 11/2003 | Chun et al. |
| 2004/0024452 A1 | 2/2004 | Kruse et al. |
| 2004/0073297 A1 | 4/2004 | Rohde et al. |
| 2004/0098098 A1 | 5/2004 | McGuckin, Jr. et al. |
| 2004/0137042 A1 | 7/2004 | Hiles et al. |
| 2004/0167619 A1 | 8/2004 | Case et al. |
| 2004/0180042 A1 | 9/2004 | Cook et al. |
| 2004/0186558 A1 | 9/2004 | Pavcnik et al. |
| 2004/0225352 A1 | 11/2004 | Osborne et al. |
| 2005/0143807 A1 | 6/2005 | Pavcnik et al. |
| 2005/0267560 A1 | 12/2005 | Bates |
| 2005/0273160 A1 | 12/2005 | Lashinski et al. |
| 2006/0020332 A1 | 1/2006 | Lashinski et al. |
| 2006/0020334 A1 | 1/2006 | Lashinski et al. |
| 2006/0111770 A1 | 5/2006 | Pavcnik et al. |

VALVE DEVICE WITH INFLATABLE CHAMBER

RELATED APPLICATIONS

This application is a division of U.S. Non-provisional application Ser. No. 11/394,303, filed on Mar. 30, 2006 and which claims the benefit of U.S. Provisional Application No. 60/666,791, filed on Mar. 31, 2005. Each of these related applications is hereby incorporated into the current application in its entirety.

FIELD OF THE INVENTION

The present invention relates to medical devices, and in particular to prosthetic valve devices, methods of making such devices, and methods of deploying such devices within a body vessel.

BACKGROUND OF THE INVENTION

By use of a closed circulatory system, animal bodies use many internal organs and vessels to transport fluids from one bodily location to another. Components of the circulatory system include the heart, blood vessels, and blood. The heart has valves (semilunar valves and atrioventricular valves) that regulate the flow of blood in the atria and the ventricles. Three examples of blood vessels are arteries, veins, and capillaries. Whereas arteries transport blood to organs throughout the body (i.e., away from the heart), veins carry blood back to the heart. Structurally, capillaries have an inner endothelium surrounded by a membrane, while arterial and venal walls have three layers: connective tissue forms the outer layer, while smooth muscle having elastic fibers forms the middle layer, and there is an innermost endothelium layer. Mammalian veins, such as human veins for example, have naturally occurring valves positioned along the length of the vessel.

Mammalian valves, such as human venous valves for example, act as one-way check valves that open to permit the flow of a fluid in a first direction (e.g., muscles contract, squeeze the veins, and the valves—flaps of tissue—keep blood moving toward the heart), and quickly close upon a change in pressure, such as a transition from systole to diastole or when muscles relax or stop contraction, to substantially prevent fluid flow in a reverse direction, i.e., retrograde flow.

While natural valves may function for an extended time, some may lose effectiveness, which can lead to physical manifestations and pathology. For example, venous valves are susceptible to becoming insufficient due to one or more factors. Over time, the vessel wall may stretch, affecting the ability of valve leaflets to close. Furthermore, the leaflets may become damaged, such as by formation of thrombus and scar tissue, which may also affect the ability of the valve leaflets to close. Once valves are damaged, venous insufficiency may be present and can lead to discomfort and possibly ulcers in the legs and ankles.

Current treatments for venous insufficiency include the use of compression stockings that are placed around the leg of a patient in an effort to force the vessel walls radially inward to restore valve function. Surgical techniques are also employed in which valves can by bypassed or replaced with autologous sections of veins with competent valves.

Minimally invasive techniques and instruments for placement of intraluminal medical devices have developed over recent years. A wide variety of treatment devices that utilize minimally invasive technology has been developed, including stents, stent grafts, occlusion devices, infusion catheters and the like. Minimally invasive intravascular devices have especially become popular with the introduction of coronary stents to the U.S. market in the early 1990s. Prosthetic valves that mimic the function of natural valves have proven successful in treating venous insufficiency.

It is desirable to have prosthetic valve devices with inflatable frames for implantation in a body vessel as taught herein, methods of making such devices, and methods of deploying such devices in a body vessel.

BRIEF SUMMARY OF THE INVENTION

In one embodiment of the present invention, a valve device for implantation in a body vessel is provided. The valve device includes at least one flexible member that permits fluid flow in a first direction and substantially prevents fluid flow in a second direction. The flexible member has a proximal portion and a distal portion. The valve device also includes an inflatable chamber at least partially attached to the proximal portion of the flexible member. The inflatable chamber is adapted to receive inflating media. A portion of the inflatable chamber contacts the body vessel to hold the chamber in the body vessel.

In another embodiment, a delivery system is provided for implanting a prosthetic valve in a body vessel. The delivery system includes a prosthetic valve and a delivery apparatus. The prosthetic valve includes at least one flexible member that permits fluid flow in a first direction and substantially prevents fluid flow in a second direction and an inflatable chamber at least partially attached to the flexible member. The inflatable chamber is adapted to receive inflating media and for engaging the body vessel. The delivery apparatus includes a member for filling the chamber with the inflating media.

In another embodiment, a method of making a prosthetic valve for implantation into a body vessel is provided. The method includes providing a flexible, main body member having an outer edge, folding over the outer edge onto the main body member, and attaching the folded-over outer edge to the main body member to form an inflatable chamber around at least a portion of a circumference of the body member. The inflatable chamber includes an opening adapted to receive inflating media. At least one flexible member is provided for at least partial connection to the main body member. The at least one flexible member is movable between a first position that permits fluid flow in a first direction and a second position that substantially prevents fluid flow in a second direction.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE INVENTION

The present invention relates to medical devices, and in particular to prosthetic valves with inflatable frames for implantation in a body vessel, preferably a vascular vessel, methods of making such valves, and delivery systems for such valves to a body vessel. For example, the valves of the present invention are suitable for implantation into the vessels of the vasculature, such as veins, for regulating fluid flow through the vessel. The valves of the present invention may also be implanted in a passageway of the heart to regulate the fluid flow into and out of the heart. As used herein, the term "implantable" refers to an ability of a medical device to be positioned at a location within a body, such as within a body vessel, either temporarily, semi-permanently, or permanently. Permanent fixation of the valve device in a particular position is not required. Furthermore, the terms "implantation" and "implanted" refer to the positioning of a medical device at a location within a body, such as within a body vessel.

For the purposes of promoting an understanding of the principles of the invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein the terms comprise(s), include(s), having, has, contain(s) and the variants thereof are intended to be open ended transitional phrases, terms, or words that do not preclude the possibility of additional steps or structures.

Figure 1A:
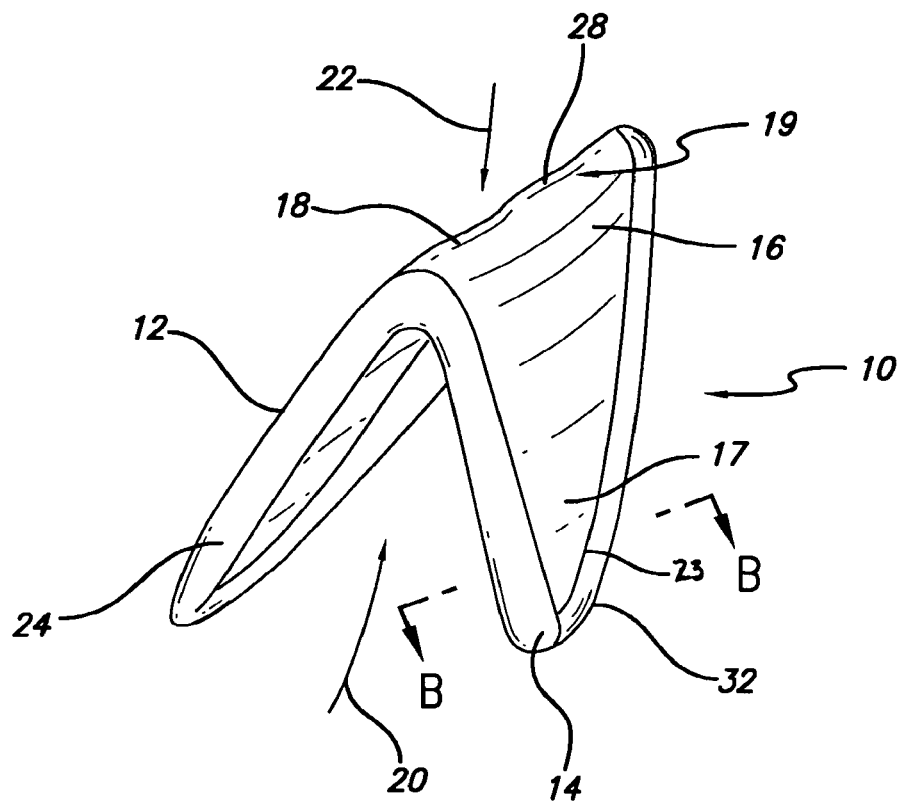
FIG. 1A is a perspective view of an embodiment of the inflatable valve device of the present invention.

As illustrated in FIG. 1A, a prosthetic valve device 10 of an embodiment of the present invention includes a valve portion 12 having an edge 14, a leaflet 16 that includes a proximal portion 17 attached to at least a portion of the edge 14 and a distal portion 19 at an opening 18 in the valve portion 12. The opening 18 allows fluid flow in a first direction 20 through the valve device 10 and restricts fluid flow in a second, generally opposite flow direction 22. In some embodiments, the valve portion 12 may not include a leaflet. For example, the valve portion 12 may be tubular in shape or include a structure other than a leaflet that is adapted to open and close in response to the fluid flow in the first direction 20 and the second direction 22 respectively.

Figure 1B:
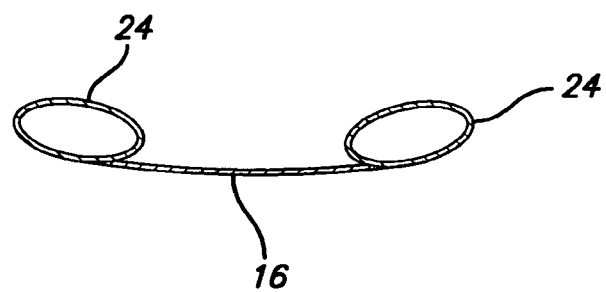
FIG. 1B is a cross-sectional view of a portion of the embodiment shown in FIG. 1A.
Figure 2A:
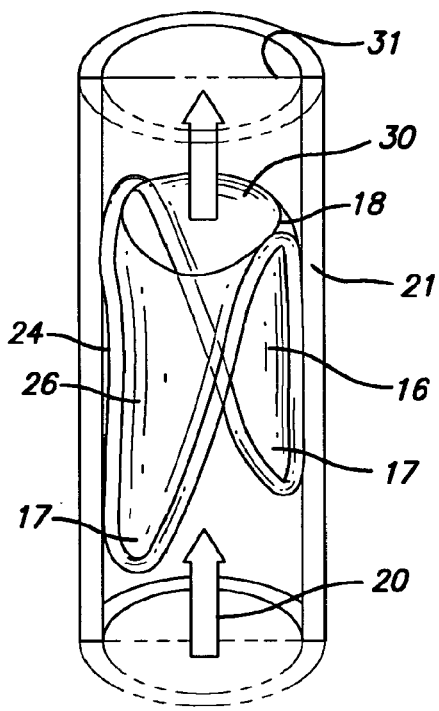
FIG. 2A is side view of a valve device in the open position in a vessel.
Figure 5:
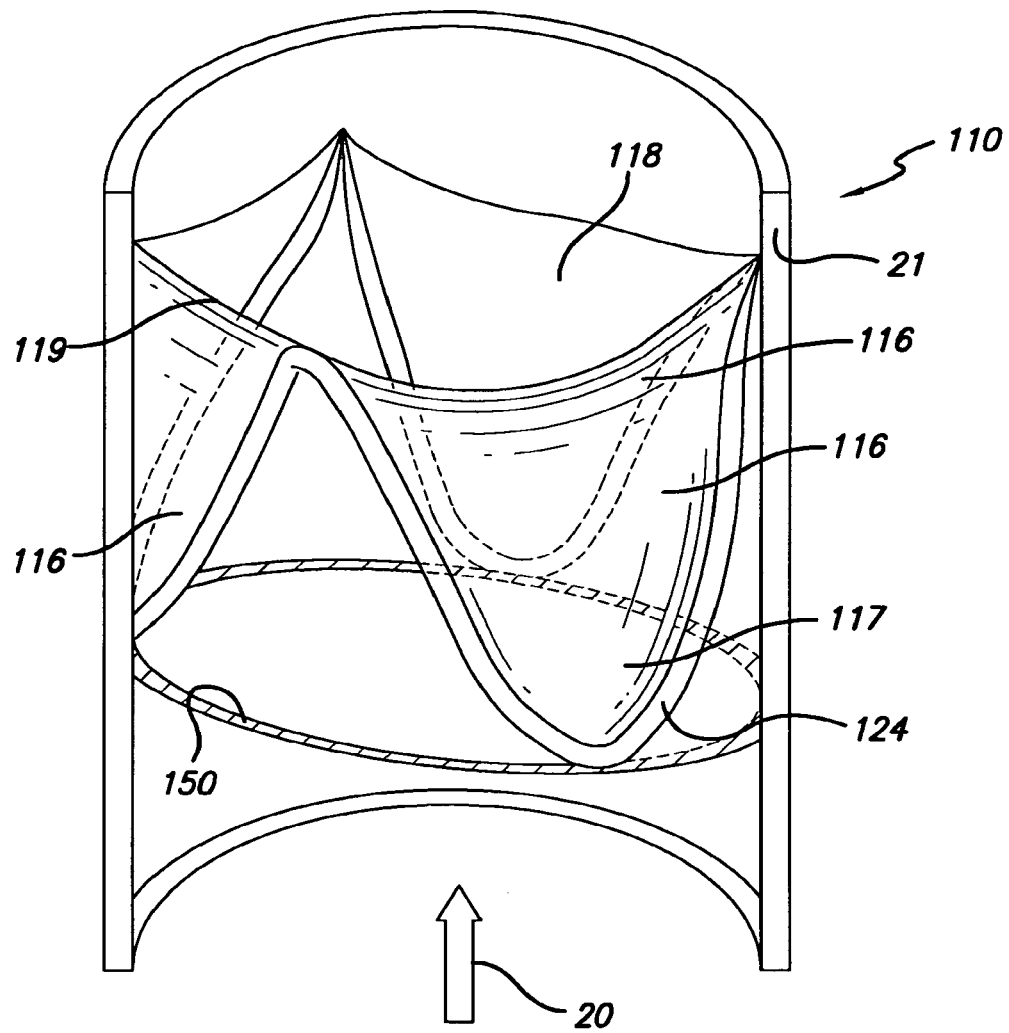
FIG. 5 is a perspective view of an alternative embodiment of the valve device.
Figure 7:
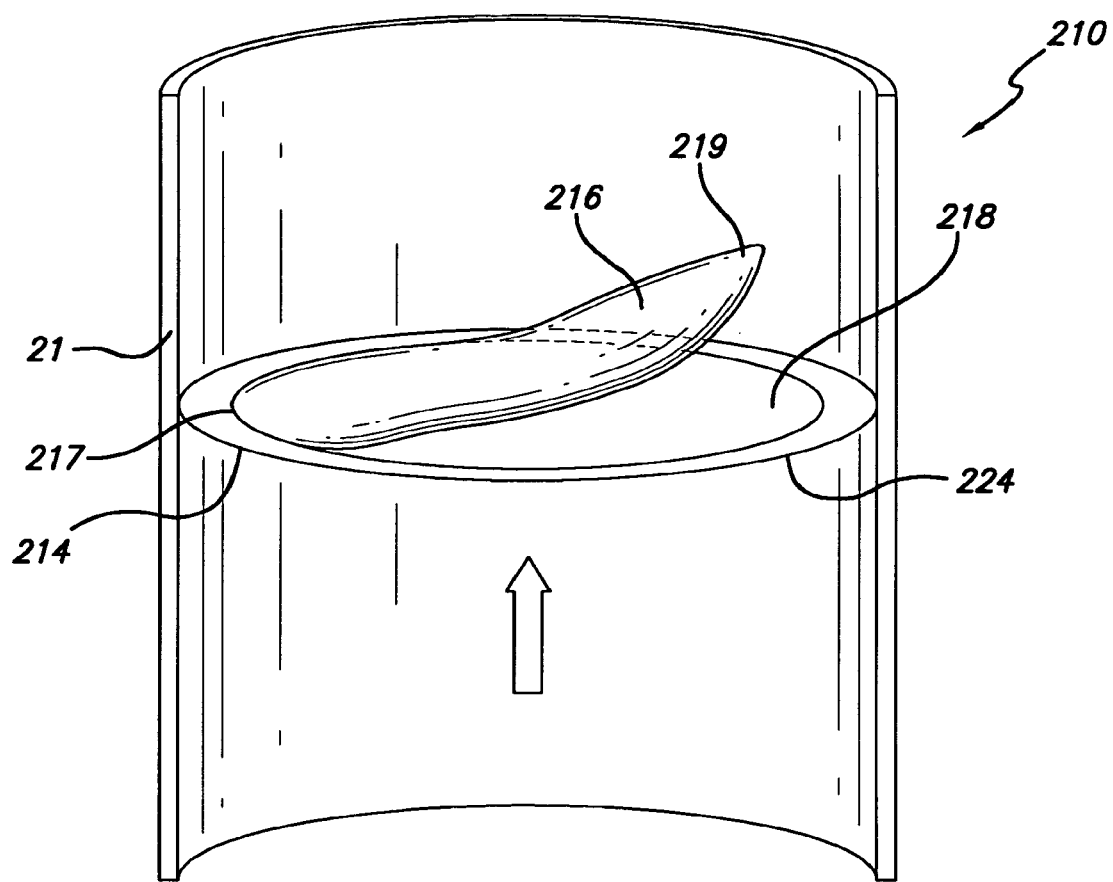
FIG. 7 is a perspective view of an alternative embodiment of the valve device.

As shown in FIG. 1A, the valve device 10 further includes an inflatable chamber 24 formed at the edge 14 of the valve portion 12. In some embodiments, the inflatable chamber 24 may be coextensive with at least a portion of an outer edge 23 of the leaflets 16. In some embodiments, the inflatable chamber 24 may coextend with the leaflets 16 and surround the entire valve portion 12 along the edge 14. Alternatively, the inflatable chamber 24 may be formed on a portion of the edge 14 of the valve device 10. In some embodiments, the inflatable chamber 24 may also extend across the leaflets 16 as well as being coextensive with the edge 23 of the leaflets 16 (see FIG. 3). A cross-sectional view of the inflated chamber 24 is shown in FIG. 1B with the chamber 24 inflated. The embodiment shown in FIG. 1A preferably includes a first leaflet 16 and a second leaflet 26. One of skill in the art will understand that the valve device 10 may include any number of flexible members that may respond to fluid flow through the valve device 10. For example, one leaflet, or a plurality of leaflets, e.g. two, three, four, five or more leaflets may be included. (See, for example, FIG. 5, showing three leaflets, and FIG. 7 showing one leaflet.) The leaflets 16, 26 may be formed with a flexible material and move outwardly to open the opening 18 when subjected to fluid flow in the first direction 20 in a vessel 21, as shown in FIG. 2A. The leaflets 16, 26 may move inwardly to substantially close the opening 18 when subjected to fluid flow in the second direction 22 in the vessel 21, as shown in FIG. 2B.

Figure 2B:
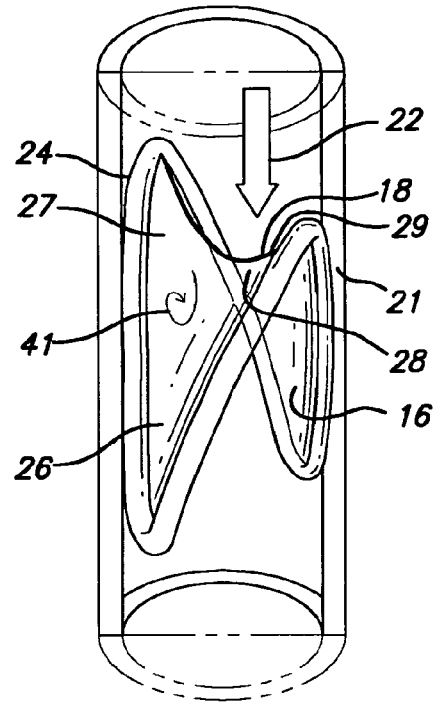
FIG. 2B is a side view of the valve device of FIG. 2A in the closed position in a vessel.

The leaflets 16, 26 may contact each other at a leaflet contact area 28 at a distal portion 29 of the valve device 10, shown in FIG. 2B. The leaflet contact area 28 comprises a longitudinal portion along the valve device 10 in which the facing surfaces of leaflets 16, 26 coapt or lie in close proximity to one another. The leaflets 16, 26 may be shaped and sized to provide a sufficient leaflet contact area 28 to decrease the amount of retrograde flow in the second direction 22 through the opening 18 as compared to damaged valves. One of skill in the art will understand how to maximize the leaflet contact area 28, for example, by lengthening the leaflets 16, 26 longitudinally with respect to the diameter of the vessel 21 into which the valve device 10 is implanted. By extending the leaflet contact area 28, the valve device 10 may substantially seal during retrograde flow in the direction 22 so that undesired retrograde flow through the opening 18 may be minimized. Any configuration for the leaflets 16, 26 that reduces undesired retrograde flow through the opening 18 may be used in the present invention.

As shown in FIGS. 2A and 2B, the proximal portion 17 of the leaflets 16, 26 are attached to the chamber 24 and the chamber 24 engages the vessel 21. The attachment of the proximal portion 17 of the leaflets 16, 26 to the chamber 24 and the engagement of the wall 21 may form a sealing engagement such that fluid substantially flows through the opening 18 in the valve device 10 and not between the chamber 24 and the wall 21. Together the chamber 24 and the proximal portions 17 of the leaflets 16, 26 form sinuses 27 similar to natural sinuses formed by native valves. The sinuses 27 prevent fluid flow in the second direction by trapping fluid flow between the leaflets 16, 26 and the vessel 21 and the fluid in the sinuses 27 pushes the leaflets 16, 26 together and away from the vessel 21 to contact each other at the opening 18. The sinuses 27 help to create flow vortices 41 to prevent fluid from pooling or stagnating in the sinuses 27. Stagnation of the fluid in the sinuses 27 may lead to thrombosis or other problems. One of skill in the art will understand that the leaflets 16, 26 will be sized and shaped to provide sufficient coaptation and to minimize stagnation of fluid flow in the sinuses 27 formed between the leaflets 16, 26, the chamber 24 and the vessel wall 21.

The size of the valve device 10 will depend on the size of the body vessel into which the valve device 10 will be implanted. The expanse of the leaflets 16, 26 at the opening 18 will vary depending on the size of the valve device 10 as well as the length of the leaflet contact area 28. In an average sized valve device 10 having a length of 25 mm, the preferred range of the coaptable leaflet contact area 28 may comprise 10-80% of the valve device 10 length (2.5-20 mm). A more preferred leaflet contact area 28 may comprise 30-60%, with 35-55% being most preferred. The relationship between leaflet contact area 28 and the diameter of the vessel 21 may be a factor in optimizing the functionality of the valve device 10. Preferably, the length of the leaflet contact area 28 is 25-250% of the nominal vessel diameter, with a more preferred range of 25-150%.

In some embodiments, the valve device 10 is configured such that the distance formed between the leaflets 16, 26 in their fully open position 30 and the vessel diameter 31 remains preferably between 0-100% of the vessel diameter 31, with a more preferred range of 20-80% of the vessel diameter 31, and a most preferred range of 50-70% of the vessel diameter 31. In addition, the amount of slack in the leaflet 16, 26 material also helps to determine how well the leaflets 16, 26 coapt during retrograde flow in the second direction 22 and how large of an opening 30 the leaflets 16, 26 permit during flow in the first direction 20. The leaflets 16, 26 may be sized and shaped so that regular contact the outer walls of the vessel 21 may be diminished, especially when the leaflets 16, 26 are formed from a bioremodelable material, such as an ECM, which can partially adhere to the wall of the vessel 21 over time as tissue grows into the leaflets 16, 26, thus compromising the functionality of the valve device 10.

The valve device 10 may be formed from biocompatible material, described below. The edge 14 forming the chamber 24 and the leaflets 16, 26 may be formed from the same material or different materials. By way of example, but not limited to the following, the chamber 24 may be formed in the edge 14 by folding, rolling, or otherwise gathering and securing material for example by sewing, adhering, heat sealing, tissue welding, weaving, cross-linking, or otherwise suitable means for joining at the periphery of the material from which the leaflets 16, 26 are made, thereby forming a one piece valve device 10. Alternatively, a different material may be secured to the periphery of the leaflets 16, 26 to provide the chamber 24 in the edge 14. When the chamber 24 is formed separately from the leaflets 16, 26, the chamber 24 may be secured to the leaflets 16, 26 by sewing, adhering, heat sealing, tissue welding, weaving, cross-linking, or otherwise suitable means for joining the chamber 24 to the leaflets 16, 26.

In some embodiments, materials such as biocompatible polyurethane i.e., THOALON, and/or extracellular matrix materials (ECM) may be used to form a portion of the valve device 10 (materials described in more detail below). For example, when THORALON is used for form the chamber, the chamber may be formed using a mandrel to form a tube-like structure or to form the desired shape of the chamber for implantation. Leaflets may be formed from THORALON and a portion of the leaflets attached to the chamber, for example by solvent bonding or by any method known to one skilled in the art. Additional materials for the leaflets may also be used and connected to the chamber. Similarly, when ECM is used, the chamber may be formed on a mandrel in any desired size and shape. ECM may also be used to form the leaflets into any size and shape. A portion of the leaflets may be connected to the chamber by any method known to one skilled in the art. Alternatively, the ECM may be formed as a sheet and one or more edges of the sheet may be rolled and connected to the sheet to form the chamber and an opening may be made in the sheet between the rolled edges to form an opening of the valve device. Additional combinations of materials and methods for forming the chamber and the leaflets may also be used to form the valve device of the present invention.

Additionally, portion of the valve device 10 may be strengthened or made less permeable by molding or overlaying the device 10 with an additional layer of biocompatible material. Alternatively, the chamber 24 or the leaflets 16, 26 or portions thereof may be strengthened or made less permeable by molding or overlaying with an additional layer of biocompatible material.

Figure 3:
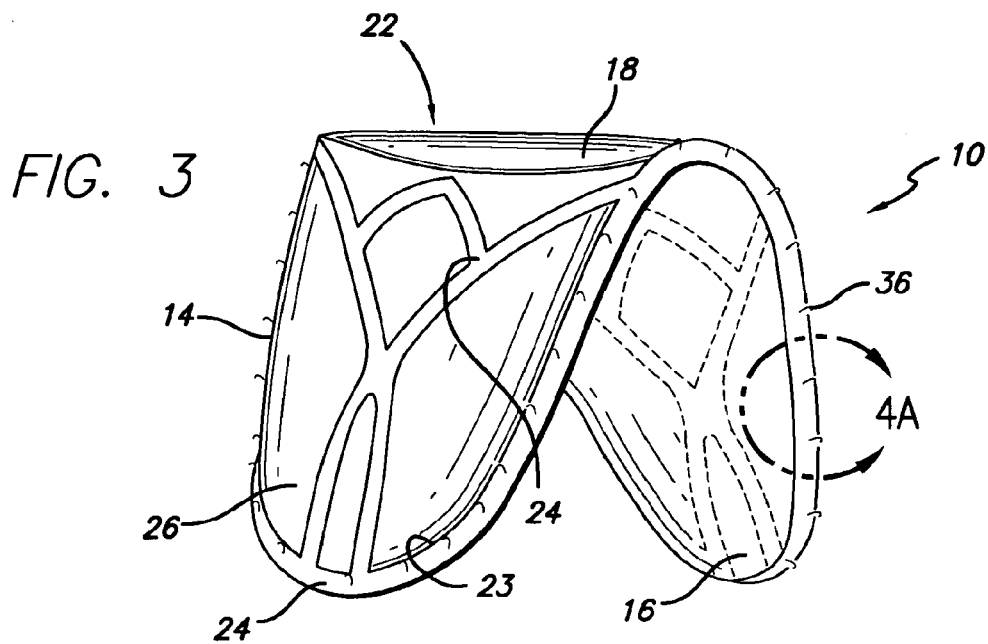
FIG. 3 is a perspective view of the embodiment of FIG. 1 having attachment elements.
Figure 6:
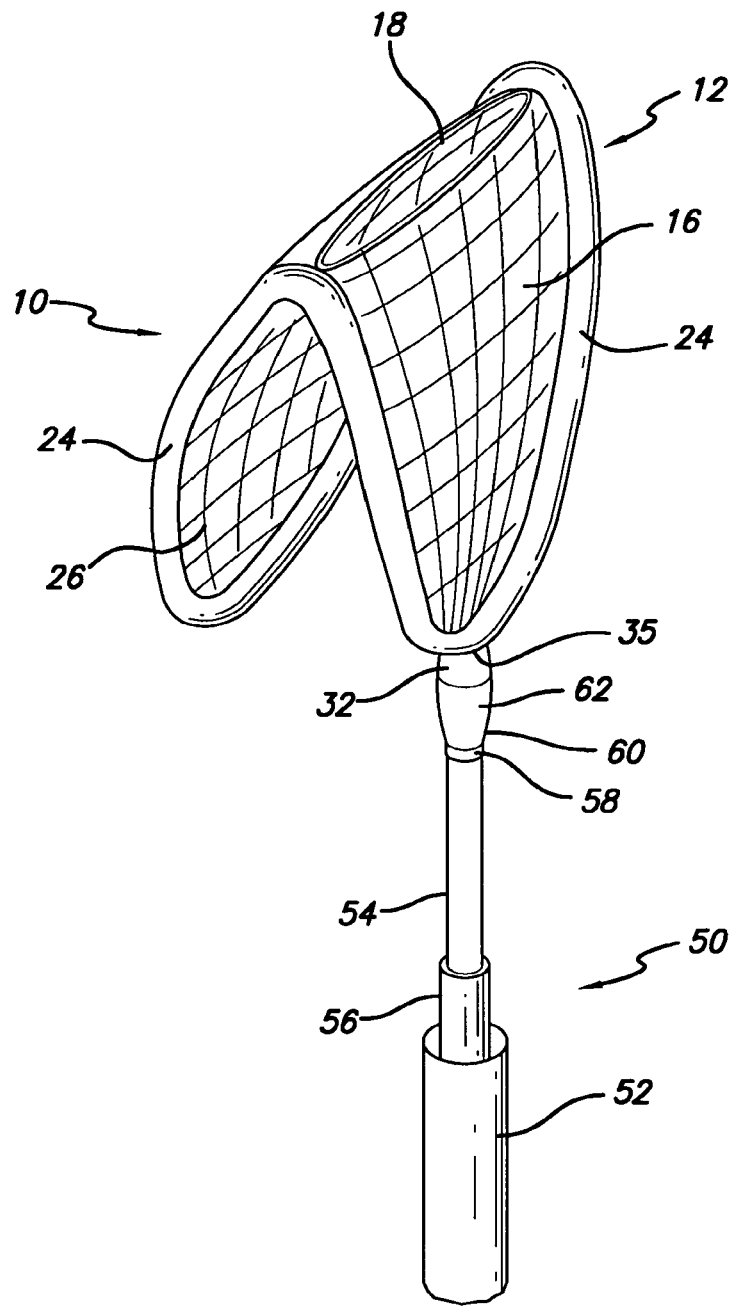
FIG. 6 is a side view of an embodiment of the valve device and a delivery apparatus.

In some embodiments, when the chamber 24 is formed in the edge 14, an opening 35 may be left unjoined to provide an aperture for injecting media into the chamber 24 for inflation of the chamber 24 during placement of the valve device 10 in a body vessel as described below. Alternatively, the opening 35 may be provided in the chamber 24 after the chamber 24 is formed, for example, by cutting, heating or otherwise opening a portion of the chamber 24. When the chamber also extends across the leaflets 16 as shown in FIG. 3, the chamber 24 may be formed as a unitary chamber and filled across the leaflets at the same time as the edge of the chamber. Alternatively, portions of the chamber may be filled separately, each portion having its own opening. A fill valve 32 may be included at the opening 35 in the chamber 24. The valve 32 is shown in FIG. 6. The chamber 24 may be formed so that chamber 24 may be sealed after the chamber 24 has been inflated to prevent leakage of the media injected into the chamber 24 into the body vessel 21 and undesired deflation of the chamber 24. In some embodiments, the valve 32 is a self-sealing valve that will allow the chamber to be inflated in situ without the risk of unwanted deflation. Alternatively, the valve 32 may allow for some deflation of the valve device 10 to correctly size the valve 32 for the vessel 21 into which the valve 32 is placed. Deflation of the valve may occur by removing some of the injected media through a filling tube 62 (described below) or when a biocompatible, liquid media is used, the media may be released into the circulation of the patient or into the delivery catheter.

The inflatable chamber 24 and valve portion 12 may assume any shape suitable for prosthetic valves that are implanted into a body vessel. For example, the cross-section of the inflatable chamber 24 may be circular, square, rectangular, triangular, any polygonal shape, crescent, oval, D-shaped, T-shaped, U-shaped, or any configuration to accommodate the valve portion forming a valve for implantation in a body vessel. In addition, the valve device 10 may be inflated to form a valve having a shape similar to prosthetic valves known in the art, including, but not limited to shapes resembling valves having stents, where the shape may be braided strands, helically wound strands, ring members, consecutively attached ring members, zig-zag members, loops, and tubular members, as will be understood by one of skill in the art. In some embodiments, a chamber 224 of a valve device 210 may be formed in a ring-like structure that attaches to the vessel wall 21 and includes a leaflet 216 that covers the opening 218 formed in the valve device 210 as shown in FIG. 7.

Exemplary techniques for attachment include physical adaptations such as barbs or hooks, suturing, stapling, bonding, gluing or otherwise adhering the valve 10 to the vessel wall 21 or combinations thereof. For example, the valve 10 may be secured in place with a tissue adhesive between the valve 10 and the vessel wall 21. Examples of tissue adhesives include, but are not limited to, fibrin glues, TISSEEL®, FLOSEAL®, BIOGLUE®, THOREX®, polyethylene glycol, and bovine or human derived thrombin, fibrinogen, and collagen. The attachment portion 46 may be secured to the vessel 21 with bioresorbable sealants and adhesives. Examples of bioresorbable sealants and adhesives include FOCALSEAL®. (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by MediWest Pharma; and VETBOND® which consists of n-butyl cyanoacrylate produced by 3M.

The edge 14 of the valve device 10 may alternatively or additionally include adaptations for attachment to the vessel wall 21. As shown in FIG. 3, the edge 14 may include a plurality of elements 36 configured to partially or completely penetrate the body vessel walls, for example barbs or hooks. The adaptations for attachment to the vessel wall may be provided on a portion of the edge 14 or the adaptations may be on the entire periphery defined by the edge 14. As will be understood by one of skill in the art, the number of adaptations and portion of the edge 14 including adaptations will be sufficient to secure the valve device 10 to the vessel 21 temporarily, semi-permanently or permanently.

Figure 4A:
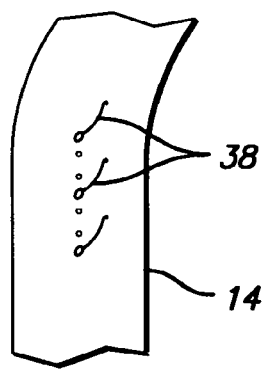
FIG. 4A is an enlarged view of an attachment element having barbs.
Figure 4B:
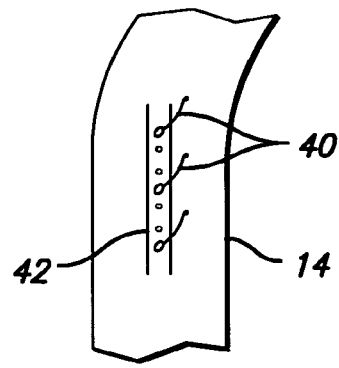
FIG. 4B is an enlarged view of an attachment element having barbs secured to a wire.
Figure 4C:
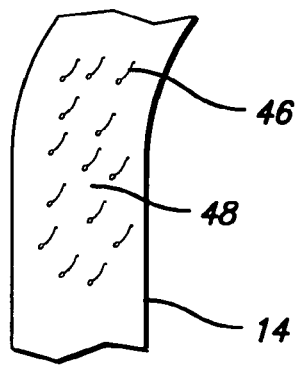
FIG. 4C is an enlarged view of an attachment element having hooks.

As shown in FIGS. 4A-C, exemplary elements 36 for attachments are provided. In FIG. 4A, individual barbs 38 are provided. The barbs 38 may be individually secured to the edge 14 by any means known to one of skill in the art, including but not limited to stitching and adhesive. In FIG. 4B, barbs 40 may be provided along a wire element 42, with each barb 40 being spaced apart along the wire element 42. The wire element 42 may then be secured to the edge 14, for example by stitching the wire 42 including the barbs 40 to the edge 14 or applying adhesive the wire 42 and securing to the edge 14. The wire element 42 itself, in this embodiment, does not constitute a stent, as the wire element 42 itself does not serve to exert radial force upon the vessel wall to retain the position of the device as would a stent. FIG. 4C illustrates a plurality of hooks 46 along the edge 14 for attachment of the valve device to the vessel wall. As shown in FIG. 4C, a plurality of small, closely spaced vessel wall-penetrating hooks 46 extend from the edge 14. The hooks 46 may be provided in a regular or irregular array, preferably two or more hooks wide as well as extending longitudinally along the edge 14. Preferably, the hooks 46 are provided on a wire element 48 that may be attached to the edge 14 of the valve device 10. The hooks 46 and the wire element 48 may be stitched or adhered to the edge 14 by any method known to one of skill in the art. As described above, the wire element 48 does not constitute a stent. Additional attachment configurations and delivery methods may be found in WO 04/089253 which is herein incorporated by reference in its entirety.

In some embodiments, a frame 150 may be provided with a valve 110 as shown in FIG. 5. The valve 110 is shown after inflation of the chamber 124 and implantation into the vessel 21. The valve 110 includes three leaflets 116 shown in an open configuration with fluid flow in the first direction 20 through the opening 118. In embodiments including the frame 150, a portion of the edge 14 may be connected to the frame 150 and to the vessel 21. In some embodiments, the frame 150 may be self-expanding or balloon-expandable. Alternatively, the frame 150 may be inflatable, either as a separate inflatable portion from the chamber 124 or the frame 150 may be connected to the chamber 124 such that when the chamber is inflated, the frame 150 also inflates. The frame 150 may be in the shape of a ring-like structure, although any shape and size frame 150 may be used for implantation into a vessel wall 21. The frame 150 can be formed from any suitable material that provides a desired amount of flexibility and resiliency. For example, the frame member 150 can be an annular ring, a molded polymer conduit, a rolled or reinforced portion of material, a woven section of material, an implantable frame having any suitable structure, or any combination thereof. The frame 150 can have any suitable size. The exact configuration and size chosen will depend on several factors, including the desired delivery technique, the nature of the body vessel in which the valve 110 will be implanted, and the size of the vessel. The frame 150 can be sized so that a second, expanded configuration is slightly larger in diameter that the inner diameter of the vessel in which the medical device will be implanted. This sizing can facilitate anchoring of the valve 110 within the vessel wall 21 and maintenance of the valve 110 at a point of treatment following implantation.

Examples of suitable frames 150 for use in the valve of the present invention include those described in U.S. Pat. Nos. 6,508,833; 6,464,720; 6,231,598; 6,299,635; 4,580,568; and U.S. Patent Application Publication Nos. 2004/018658 A1 and 2005/0228472 A1, all of which are hereby incorporated by reference in their entirety.

The valve 10 may further include one or more imagable materials located on the valve 10 that are configured to facilitate placement of the valve 10 in the vessel wall 21 in the desired orientation. The imagable materials may be viewed by devices such as a fluoroscope, X-ray, ultrasound, M.R.I., and others known to one of skill in the art. For example, radiopaque substances containing tantalum, barium, iodine, or bismuth, e.g. in powder form, can be coated upon or incorporated within the materials used to form the valve 10, such that, the location of the valve 10 is detectable. Exemplary prosthetic valve devices and imagable materials are further described in U.S. Publication No. 2004/0167619, which is incorporated by reference herein in its entirety.

As shown in FIG. 6, the valve device 10 may be delivered to the vessel using a deployment apparatus 50, by way of non-limiting example, a delivery catheter known to one of skill in the art. Exemplary deployment apparatuses are described in U.S. Patent Application Publication Nos. 2004/0225322 and 2003/0144670, which are herein incorporated by reference in their entirety. Alternatively, rapid exchange catheters may be used, such as a rapid exchange delivery balloon catheter which allows exchange from a balloon angioplasty catheter to a delivery catheter without the need to replace the angioplasty catheter wire guide with an exchange-length wire guide before exchanging the catheters. Exemplary rapid exchange catheters that may be used to deliver the valve device of the present invention are described in U.S. Pat. Nos. 5,690,642; 5,814,061; and 6,371,961 which are herein incorporated by reference in their entirety.

The deployment apparatus 50 may include an outer sheath member 52, an inner catheter member 54 and a coaxial pushing member 56. The deployment apparatus 50 may further include a tethering tip 58 extending from the inner catheter member 54. The tethering tip 58 may be adapted to receive an extension 60 from the chamber 24 of the valve device 10. The extension 60 may be a filler tube 62 for connecting to the valve 32. As will be understood by one of skill in the art, the valve 32 may be formed in the chamber 24 such that the valve 32 is flush with the exterior of the chamber 24 and no extension 60 is necessary (see FIG. 1A). As described above, the valve 32 may be a one-way valve that seals upon removal of the inner catheter member 54. The valve 32 may include a male or a female part to connect with the filling tube 62 having the alternative female or male part for connection thereto.

In some embodiments, the valve device 10 may be adapted to be collapsible to fit within the lumen of the deployment apparatus 50, the deployment apparatus 50 is then introduced into the body vessel and a tip of the deployment apparatus 50 is positioned at a point of treatment within the vessel. The valve device 10 may be expelled from the deployment apparatus 50 and the chamber 24 inflated. As shown in FIG. 6, the valve device 10 is expelled from the deployment apparatus 50 and the tethering tip 58 maintains the valve device 10 on the inner catheter member 54 for filling of the chamber 24. The chamber 24 may be inflated with the inflation media through the inner catheter member 54 which may expand the edge 14 of the valve device 10 until the edge 14 contacts and engages the vessel 21. The attachment elements, adhesive or both may secure the valve device 10 in position for implantation of the valve device 10 in the vessel 21.

One of skill in the art will understand the amount of inflation of the chamber 24 that will be necessary for implantation of the valve device 10 in the vessel 21. In some embodiments, the inflation media includes a polymerizing matrix of biocompatible material that solidifies or semi-solidifies in the chamber 24. For example, the inflation media may include a polymerizing matrix and SIS. Depending on the polymerization time of the matrix, the inflating media may be injected and partially withdrawn in to the tubing 62 to ensure proper placement and securing force in the vessel 21. The valve 10 may remain flexible after inflation and securing to the vessel 21 to be movable as the vessel 21 changes in shape, i.e., in response to changes in blood flow and to changes in body position. After completion of the inflation of the chamber 24, the tethering tip 58 may be pushed off the inner catheter member 54 by advancing the catheter 56 while applying counter traction on the inner catheter 54. When the inner catheter 54 is withdrawn from the valve 32, the valve 32 may automatically seal. The deployment apparatus 50 may then be removed from the vessel 21. Alternatively, the chamber may be inflated or partially inflated prior to delivery to the body vessel. In some embodiments, the inflating media may be solidified once the valve is placed in the vessel 21.

FIG. 7 illustrates the valve device 10 after inflation of the chamber 24 with the inflation media and after release from the deployment apparatus 50.

As described above, the valve device 10 includes a chamber 24 that may be inflated using inflating media injected through the valve 32. The inflating media for the chamber 24 includes any suitable material for injection into the chamber 24 upon implantation in a body vessel 21, such that, upon injection, the inflating media exerts radial pressure upon the inner surface of the inflatable chamber 24 that is greater than the pressure that the body vessel wall 21 exerts upon the outer surface of the inflatable chamber 24. In this way, injection of the inflating media causes the inflatable chamber 24 to expand and engage the vessel wall 21. The engagement of the chamber 24 with the vessel wall 21 may be sufficient to substantially prevent fluid flow between the chamber 24 and the vessel wall 21 where the chamber 24 engages the wall 21 after inflation. The optimal radial pressure that the entire valve device 10 exerts on the body vessel wall 21 is one at which at least a portion of the valve device 10 conforms to the vessel wall 21 and substantially prevents retrograde flow in the direction 22 without causing erosion or damage to the vessel wall 21 that could lead to rupture.

Suitable inflating media include, but are not limited to, any biocompatible materials, including resorbable materials. Non-limiting examples of inflating media may include a gases, solids, liquids, gels, or foams, such as a collagenous fill material, a remodelable or absorbable material, a biocompatible polymer, an aqueous buffer such as saline, a non-resorbable material, ECM rods or particulates, a collagenous or gelatinous foam, air, chitosan, gelatin, oxidized regenerated cellulose, calcium alginate, alginate, thrombin-fibrin enhanced materials, fibrin glues, or any suitable combination. In some embodiments, the inflating media includes ECM material that gels after injection into the inflatable chamber 24. The material may be comminuted, fluidized, and/or gelatinous remodelable material. Alternatively, the inflation media may remain flowable and may be removable or partially removable from the chamber 24 for deflation of the chamber 24. The inflation of the chamber 24 may utilize both flowable and solidifying inflation media.

Fluidized compositions suitable for use as inflating media, such as a remodelable gel, have been described in U.S. Pat. Nos. 5,275,826; 6,206,931; and 6,444,229.

Briefly, by way of example, ECM material may be prepared for use as inflating media in the present invention as follows. ECM material may be used as soluble material by digestion of the ECM material in an acidic or basic medium and/or by contact with an appropriate enzyme or combination of enzymes. Solubilization may be enhanced by first reducing the ECM material to particulate form. Reduction of the ECM material may be achieved by tearing, cutting, grinding or shearing the isolated ECM material by methods known to one of skill in the art.

Next, the ECM material may be subjected to enzymatic digestion to form a hydrolysate of ECM components, for example, using serine proteases, aspartyl proteases, and matrix metalloproteases. The concentration of the enzyme used may be adjusted based on the specific enzyme used, the amount of material to be digested, the duration of the digestion, the temperature of the digestion, and the desired properties of the remodelable material to be used for inflating media. The ratio of the concentration of ECM material (hydrated) to total enzyme usually ranges from about 25 to about 125, preferably about 50 to about 75. The digestion may be conducted at any suitable temperature, preferably from about 4.degree. C. to about 37.degree. C. The length of the digestion may range from about 2 to about 180 hours. The pH of the digestion may be optimized based on the particular enzyme as will be understood by one of skill in the art. For example, about 0.1% to about 0.2% of pepsin may be used and the digestion may be conducted at about 4.degree. C. for about 24 to about 72 hours, at a pH of about 2 to 4.

After digestion, the enzymes or other disruptive agents used to solubilize the ECM material may be removed or inactivated by methods known to one of skill in the art. Removal or inactivation of the disruptive agents will assist in gel formation and stability. Nonhydrolyzed components can be separated from the hydrolyzed portions by centrifugation, filtration, or other separation techniques known in the art.

Digested, hydrolyzed ECM materials may be fractioned, for example, under acidic conditions, e.g. ranging from about 2 to about 7, or low ionic strength solutions with minimal concentrations of salts such as those usually found in buffers such as phosphate buffered saline (e.g., NaCl, KCL, Na.sub.2HPO.sub.4 or KH.sub.2PO.sub.4). The ECM hydrolysate produced by enzymatic digestion of the ECM material has a characteristic ratio of protein to carbohydrate. The ratio will be determined by the enzyme utilized and the duration of the digestion. The resulting ratio may be similar to the starting ECM material or maybe substantially different. For example, pepsin digested ECM, followed by dialysis, will form an ECM hydrolysate having a lower protein to carbohydrate ratio relative to the original ECM material.

The flowable ECM material for use as an inflating media for the valve device 10 may be formed from the digested ECM as described above. In addition, a more concentrated hydrolysate may be formed by removing water (e.g. evaporation or lyophilization).

The hydrolyzed ECM material may form a gel upon adjusting the pH of a relatively more acidic aqueous medium to about 5 to about 9, more preferably about 6.6 to about 8.0 and most preferably to about 7.2 to about 7.8. The pH of the ECM material may preferably be raised by the addition of a buffer that does not leave a toxic residue. The ionic strength of the ECM hydrolysate is believed to be important in maintaining the fibers of collagen in a state that allows for fibrillogenesis and matrix gel assembly upon neutralization of the pH of the hydrolysate. The salt concentration of the ECM may be optimized prior to the neutralization on the hydrolysate. The temperature of the gellation of the hydrolysate may range form about 4.degree. C. to about 40.degree. C., ranging in time to gellation from about 5 to about 120 minutes, with shorter gellation times at higher temperatures.

Additional components may be added to the ECM hydrolysate prior to, during or post gellation. For example, proteins, carbohydrates, growth factors, therapeutics, bioactive agents, nucleic acids, cells or pharmaceuticals may be added.

This example is meant to be non-limiting and therefore, any method known in the art for preparing ECM or any material that may be used as inflating media is acceptable for use with the present invention.

As described above, the valve device 10 may be made of any suitable biocompatible material that is pliable, strong, resilient, elastic, and flexible. The valve 10 may be made from a single material or a combination of materials. The material or materials need only be biocompatible or able to be rendered biocompatible. The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Examples of suitable materials include natural materials, synthetic materials, and combinations of natural and synthetic materials. The biocompatible material may be, but is not required to be resorbable. As used herein, the term "resorbable" refers to the ability of a material to be absorbed into a tissue and/or body fluid upon contact with the tissue and/or body fluid. The contact can be prolonged, and can be intermittent. A number of resorbable materials are known in the art and any suitable material may be used. The material may also provide a matrix for the regrowth of autologous cells.

A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, polylysine, gelatin, fibrin, fibrinogen, casein, and collagen.

Examples of biocompatible homo- or co-polymers suitable for use in the present invention include vinyl polymers including polyfumarate, polyvinylpyrolidone, polyvinyl alcohol, poly-N-(2-hydroxypropyl)-methacrylamide, polyacrylates, and polyalkylene oxalates.

Reconstituted or naturally-derived collagenous materials can be used in the present invention. Such materials that are at least bioresorbable will provide advantage in the present invention, with materials that are bioremodelable and promote cellular invasion and ingrowth providing particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5.mu.g/mg, more preferably less than about 2.mu.g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

For example, when a portion of the valve is formed from an ECM, such as small intestine submucosa (SIS), the SIS may be used in a sheet form as described above. SIS is commercially available from Cook Biotech, West Lafayette, Ind.

The valves of the present invention or portions thereof may be formed with a variety of materials, including biocompatible polyurethanes. One example of a biocompatible polyurethane is THORALON (THORATEC, Pleasanton, Calif.). As described in U.S. Pat. Nos. 4,675,361 and 6,939,377, both of which are incorporated herein by reference. THORALON is a polyurethane base polymer blended (referred to as BPS-215) with a siloxane containing surface modifying additive (referred to as SMA-300). The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates, pore forming agents or inorganic salts. Preferably the particulate is insoluble in the solvent. Examples of solvents include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18.degree. C. to about 27.degree. C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates. The particulates can then dissolve from the polymer, leaving pores in the material. It may be desirable to use warm water f. or the extraction, for example water at a temperature of about 60.degree. C. The resulting pore diameter can be substantially equal to the diameter of the salt grains.

The porous polymeric sheet can have a void-to-volume ratio from about 0.40 to about 0.90. Preferably the void-to-volume ratio is from about 0.65 to about 0.80. Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and U.S. Patent Application Publication No. 2003/0149471 A1, both of which are incorporated herein by reference.

Non-porous THORALON can be formed by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes may also be employed. These include polyurethane ureas that preferably include a soft segment and include a hard segment formed from a diisocyanate and diamine. For example, polyurethane ureas with soft segments such as polytetramethylene oxide, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

The diisocyanate used as a component of the hard segment may be represented by the formula OCN—R—NCO, where —R— may be aliphatic, aromatic, cycloaliphatic or a mixture of aliphatic and aromatic moieties. Examples of diisocyanates include tetramethylene diisocyanate, hexamethylene diisocyanate, trimethyhexamethylene diisocyanate, tetramethylxylylene diisocyanate, 4,4'-decyclohexylmethane diisocyanate, dimer acid diisocyanate, isophorone diisocyanate, metaxylene diisocyanate, diethylbenzene diisocyanate, decamethylene 1,10diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, neopentyl alcohol, 1,6-hexanediol, 1,8-octanediol, propylene glycols, 2,3-butylene glycol, dipropylene glycol, dibutylene glycol, glycerol, or mixtures thereof.

Biocompatible polyurethanes modified with cationic, anionic and aliphatic side chains may also be used. See, for example, U.S. Pat. No. 5,017,664.

Other biocompatible polyurethanes include: segmented polyurethanes, such as BIOSPAN; polycarbonate urethanes, such as BIONATE; and polyetherurethanes such as ELAST-HANE; (all available from POLYMER TECHNOLOGY GROUP, Berkeley, Calif.).

Other biocompatible polyurethanes include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Application Publication No. 2002/0187288 A1, which is incorporated herein by reference.

In addition, any of these biocompatible polyurethanes may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

Additional examples of suitable materials for portions of the valve 10 include, without limitation, stainless steel (such as 316 stainless steel), nickel titanium (NiTi) alloys, e.g., Nitinol, other shape memory and/or superelastic materials, MP35N, gold, silver, a cobalt-chromium alloy, tantalum, platinum or platinum iridium, or other biocompatible metals and/or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof, or stainless steel, polymers, and any suitable composite material.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their meaning as defined by Stedman's Medical Dictionary, 27th edition.

What is claimed is:

1. A method of implanting a valve in a body vessel having a vessel wall, the method comprising the steps of:

delivering said valve to a point of treatment within said body vessel using a deployment apparatus, said valve comprising at least one flexible member and an inflatable chamber, the at least one flexible member movable between a first position that permits fluid flow in a first direction and a second position that substantially prevents fluid flow in a second direction, the at least one flexible member at least partially attached to the inflatable chamber and having an outer edge, the inflatable chamber comprising a first portion extending along the outer edge of the at least one flexible member and a second portion extending from a first location on the outer edge, across the at least one flexible member, and to a second location on the outer edge, the inflatable chamber adapted to receive inflating media and to engage the body vessel;

inflating the first portion of the inflatable chamber with inflating media;

inflating the second portion of the inflatable chamber with inflating media, the second portion of the inflatable chamber being filled separately from the first portion of the inflatable chamber;

detaching said valve from the deployment apparatus; and removing the deployment apparatus from said body vessel.

2. The method of claim 1, wherein each of the first portion of the inflatable chamber and the second portion of the inflatable chamber has its own opening adapted to receive inflating media.

3. The method of claim 2, wherein the inflating media comprises a flowable and solidifying inflation media.

4. The method of claim 1, further comprising the step of expelling said valve from the deployment apparatus.

5. The method of claim 1, further comprising the step of removing a portion of the inflating media from the inflatable chamber.

6. The method of claim 5, wherein the portion of the inflating media removed from the inflatable chamber is released into said body vessel.

7. The method of claim 5, wherein the portion of the inflating media removed from the inflatable chamber is passed into the deployment apparatus.

8. The method of claim 1, wherein the inflating media is a biocompatible polymer.

* * * * *